United States Patent
Yang (10) Patent No.: US 9,953,413 B2
(45) Date of Patent: Apr. 24, 2018

(54) IDENTIFICATION AND ANALYSIS OF LESIONS IN MEDICAL IMAGING

(75) Inventor: Qing Yang, Melbourne (AU)

(73) Assignee: APOLLO MEDICAL IMAGING TECHNOLOGY PTY. LTD., North Melbourne (AU)

( * ) Notice: Subject to any disclaimer, the term of this patent is extended or adjusted under 35 U.S.C. 154(b) by 1865 days.

(21) Appl. No.: 12/449,310

(22) PCT Filed: Feb. 1, 2008

(86) PCT No.: PCT/AU2008/000118
§ 371 (c)(1),
(2), (4) Date: Jul. 31, 2009

(87) PCT Pub. No.: WO2008/092211
PCT Pub. Date: Aug. 7, 2008

(65) Prior Publication Data
US 2010/0066756 A1    Mar. 18, 2010

(30) Foreign Application Priority Data

Feb. 2, 2007    (AU) ................................ 2007900498

(51) Int. Cl.
*G06T 7/00* (2017.01)
*A61B 6/00* (2006.01)

(52) U.S. Cl.
CPC ............ *G06T 7/0012* (2013.01); *A61B 6/481* (2013.01); *A61B 6/504* (2013.01);
(Continued)

(58) Field of Classification Search
USPC ........ 600/407, 410, 419, 420; 382/100, 128, 382/155, 156, 157, 158, 159, 162, 164,
(Continued)

(56) References Cited

U.S. PATENT DOCUMENTS

| 6,556,856 B1 * | 4/2003 | Mistretta ............ G01R 33/5635 |
| | | 324/306 |
| 2006/0245629 A1 * | 11/2006 | Huo et al. ..................... 382/131 |

OTHER PUBLICATIONS

"Automatic identification and classification of characteristic kinetic curves of breast lesions on DCE-MRI" by W. Chen et al. Med. Phys. 33:8. pp. 2878-2887. 2006.*

(Continued)

*Primary Examiner* — Tse Chen
*Assistant Examiner* — Jason Ip
(74) *Attorney, Agent, or Firm* — Knobbe, Martens, Olson & Bear, LLP (57) ABSTRACT

A method for automated classification of curve patterns associated with dynamic image data of a lesion in a subject in order to determine characteristics of the lesion. The method comprising the steps of loading the image data into an electronic memory means, producing a plot of signal intensity profile, converting the signal intensity profile into a contrast enhancement profile, detecting a reference enhancement profile having a highly positive slope over an initial enhancement period followed by a decreasing profile portion, deriving signature curve types based on the reference enhancement profile, classifying an enhancement curve for each pixel in a selected ROI into one of the derived signature curve types using all available time points and displaying a grid-plot of the classified enhancement curves for all pixels in the selected ROI, wherein the overall display of curves and heterogeneity provides visual indication of the characteristics of the lesion.

14 Claims, 7 Drawing Sheets
(2 of 7 Drawing Sheet(s) Filed in Color)

(52) U.S. Cl.
CPC ............... *G06T 2207/10072* (2013.01); *G06T 2207/10096* (2013.01); *G06T 2207/30068* (2013.01)

(58) Field of Classification Search
USPC ................ 382/165, 181, 190, 191, 224, 225
See application file for complete search history.

(56) References Cited

OTHER PUBLICATIONS

Hoffmann et al. Pharmacokinetic Mapping of the Breast: A new method for dynamic MR Mammography. Magnetic Resonance in Medicine, Academic Press, Duluth, MN, US, vol. 33(4) Apr. 1, 1995 pp. 506-514.
Degani et al. Mapping Pathophysiology features of breast tumors by MRI at high spatial resolution. Nature Medicine, Nature Publishing Group, NY, NY, US, vol. 3(7) Jul. 1, 1997 pp. 780-782.
Evelhoch, Jeffrey L., Key Factors in the Acquisition of Contrast Kinetic Data for Oncology, Journal of Magnetic Resonance Imaging, 10:254-259, 1999.

\* cited by examiner

IDENTIFICATION AND ANALYSIS OF LESIONS IN MEDICAL IMAGING

CROSS-REFERENCE TO RELATED APPLICATIONS

The present application claims priority from Australian Provisional Patent Application No 2007900498 filed on 2 Feb. 2007, the content of which is incorporated herein by reference.

FIELD OF THE INVENTION

This invention relates to a method and system for image processing and analysis of medical imaging data, and more particularly relates to a method and system for improved identification and analysis of a lesion in dynamic medical imaging data of a subject in order to obtain desired structural and functional information by an intuitive interface coupled with automated classification of lesion enhancement patterns.

BACKGROUND OF THE INVENTION

The process of measuring functional information such as blood flow within a body of a subject non-invasively is useful in diagnosing and treating the subject. This is particularly the case where a part of a subject or patient, such as a tissue or organ, suffers from diseases due, for example, to cancer or malfunction. Identifying and analysing the characteristics of blood passing through such a tissue or organ can provide important information to medical personnel in order to determine an appropriate treatment regime for the patient.

Existing systems pertaining to the obtaining of blood flow information in vivo have been disclosed. In general, the systems involve a contrast agent that is delivered as an intravascular bolus during a dynamic imaging session such as magnetic resonance imaging (MRI), computerized tomography (CT), nuclear medicine (NM) or positron emission tomography (PET). The temporal profile of the image intensity in a pixel or region of interest (ROI) reflects the characteristics of the contrast agent and hence the blood passing through the tissue.

Figure 1:
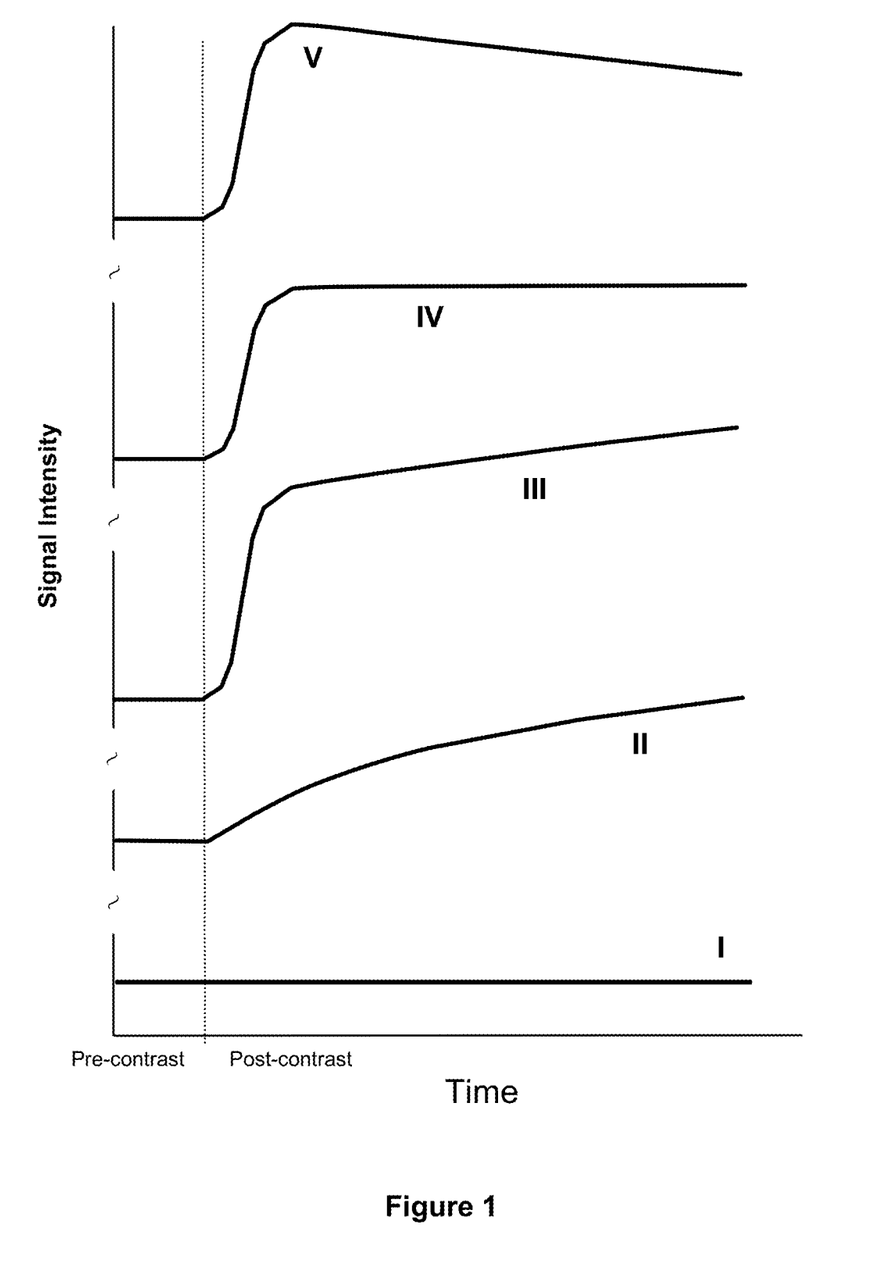
FIG. 1 illustrates five types of enhancement curves of signal intensity, as a function of time, in different breast tissues. Specifically curve I being no enhancement; curve II being slow sustained enhancement; curve III being rapid initial and sustained late enhancement; curve IV being rapid initial and stable late enhancement; and curve V being rapid initial and decreasing late enhancement.

For example, a typical breast MRI study involves at least one baseline scan before the contrast agent is injected and at least two post-contrast scans after the injection. A commonly used method for diagnostic screening of breast cancer is based on a subjective evaluation of the signal intensity time-curve of a ROI using a visual classification system. FIG. 1 shows a classification system for visual evaluation of five types of enhancement curves of signal intensity as a function of time, where the higher numbered curves are interpreted as representing more aggressive tumor types. The initial sharp rise in plots III, IV and V is due to rapid contrast enhancement. Such a classification scheme was used to achieve very good diagnostic performance in differentiating malignant from benign breast lesions (Daniel, et al. "Breast disease: dynamic spiral MR imaging", Radiology 209, pp 499-509, 1998).

A breast MRI study usually generates many hundreds of images, it can be very time consuming for medical personnel to review all the images. Methods using computer algorithms have been disclosed in an attempt to automatically detect and characterize lesions into malignant or benign classes with dynamic MRI images (see U.S. Pat. No. 6,353,803 and United States Patent Application Nos 20050074149, 20060018548 and 20060110018). In addition, lesion morphology such as architectural features identified on high spatial resolution images may reflect the underlying pathology and hence may be used to characterize lesions as benign or malignant. Methods combining kinetic and morphologic information in order to provide optimal discrimination between benign and malignant disease have also been disclosed (see U.S. Pat. No. 6,317,617 and United States Patent Application No 20060245629). However, existing methods used for classifying the enhancement curves are based on arbitrary selection of a limited number of time points, and subsequent classification based on calculated descriptive parameters are more sensitive to image noise fluctuations. Further, these methods provide no statistical significance information associated with the classification for the enhancement curve of each pixel.

Although specialist tools providing automated detection and classification of abnormalities can potentially help ease many of the image reviewing challenges, such tools are not widely available, and the reliability of such tools is yet to be validated. Most commonly used tools available from either commercial or academic software for dynamic enhancement analysis include simple subtraction, maximum intensity projection (MIP), multi-planar reconstruction (MPR) and signal intensity time-curve analysis. The time-curve analysis in everyday practice uses the region of interest (ROI) method, where the subtraction images are used to guide the ROI placement over the suspected lesion by the user, while the time-curve of the ROI average signal intensity is presented for visual evaluation and classification.

However, it should be noted that heterogeneity of curve shapes within a lesion is also diagnostically informative. A malignant tumor may well enhance with different types of curve shapes in different anatomical areas, which is a strong indicator of malignancy. The commonly used ROI method in everyday practice is prone to partial volume effects and could not effectively present such heterogeneous information to the user for detailed analysis. It is desirable for a system to provide automated classification of curve patterns with statistical significance information using all available time points of the data, coupled with simultaneous visualization of detailed spatial and temporal information in a real time fashion, which is particularly useful in a busy clinical environment.

The present invention seeks an improved method to substantially overcome or at least ameliorate any one or more of the above-mentioned disadvantages associated with automated classification and visualization of both morphologic and kinetic information in order to assist medical personnel to most efficiently characterize the lesion for optimal discrimination between benign and malignant disease.

SUMMARY OF INVENTION

According to a first aspect of the invention there is provided a method for automated classification of curve patterns associated with dynamic image data of a lesion in a subject in order to determine characteristics of the lesion, the method comprising the steps of:

(a) loading the image data into an electronic memory means;

(b) producing a plot of signal intensity profile;

(c) converting the signal intensity profile into a contrast enhancement profile;

(d) detecting a reference vascular enhancement profile having a highly positive slope over an initial enhancement period followed by a decreasing profile portion;

(e) deriving signature curve types based on the reference enhancement profile;

(f) classifying an enhancement curve for each pixel in a selected ROI into one of the derived signature curve types using all available time points; and (g) displaying a grid-plot of the classified enhancement curves for all pixels in the selected ROI, wherein the overall display of curves and heterogeneity provides visual indication of the characteristics of the lesion.

According to a second aspect of the invention there is provided a method for automated classification of curve patterns and automated segmentation of a lesion in dynamic image data of a subject, wherein the classification and segmentation results together with detailed spatial and temporal information are presented on a display means, the method comprising the steps of:

(a) loading the image data into an electronic memory means and plot on a display means signal intensity data of a region of interest (ROI).

(b) detecting the pre-contrast baseline and initial enhancement period;

(c) detecting a reference vascular enhancement profile with a strong and rapid uptake followed by late washout, and deriving signature curve types for a classification system;

(d) classifying the type of enhancement curve of every pixel in a lesion of the subject using all available time points based on a correlation analysis method;

(e) applying segmentation analysis for a lesion identified by a user defined ROI, and providing information such as the lesion volume and the percentage contribution from each type of enhancement curve.

(f) displaying a grid-plot of the curves from all individual pixels in a ROI, wherein each curve is highlighted by different color and line-thickness to reflect the type of enhancement curve and whether it is statistically significant respectively for easy visual identification;

wherein the user can easily manipulate the ROI with an intuitive interface allowing dynamic manipulation and visualization of both spatial and temporal information.

The method may further include the step of applying image registration after loading the data to compensate for motion artifacts due to movement over time of a portion of the subject, such as a tissue or organ.

The correlation analysis can be a Spearman's rank correlation, or a linear Pearson correlation or a combination of them. The type of image may be any one of MRI, CT, NM, PET or any other type of dynamic imaging methods.

According to a third aspect of the invention there is provided a system for automated classification of curve patterns associated with dynamic image data of a lesion in a subject in order to determine characteristics of the lesion, the system comprising:

scanning means for providing a dynamic image scan of the subject;

processor means linked to the scanning means for retrieving the image data from the scan;

the processor means further:

(a) loads the image data into an electronic memory means;

(b) produces a plot of signal intensity profile;

(c) converts the signal intensity profile into a contrast enhancement profile;

(d) detects a reference vascular enhancement profile having a highly positive slope over an initial enhancement period followed by a decreasing profile portion;

(e) derives signature curve types for classification of the characteristics based on the reference enhancement profile;

(f) classifies an enhancement curve for each pixel in a selected ROI into one of the derived signature curve types using all available time points; and (g) displays a grid-plot of the classified enhancement curves for all pixels in the selected ROI, wherein the overall display of curves and heterogeneity provides visual indication of the characteristics of the lesion.

According to a fourth aspect of the invention there is provided computer program means for automated classification of curve patterns associated with dynamic image data of a lesion in a subject, wherein the computer program means instructs a processor to:

(a) load the image data into an electronic memory means;

(b) produce a plot of signal intensity profile;

(c) convert the signal intensity profile into a contrast enhancement profile;

(d) detect a reference vascular enhancement profile having a highly positive slope over an initial enhancement period followed by a decreasing profile portion;

(e) derive signature curve types based on the reference enhancement profile;

(f) classify an enhancement curve for each pixel in a selected ROI into one of the derived signature curve types using all available time points; and (g) display a grid-plot of the classified enhancement curves for all pixels in the selected ROI, wherein the overall display of curves and heterogeneity provides visual indication of the characteristics of the lesion.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will hereinafter be described in a preferred embodiment, by way of example only, with reference to the drawings wherein.

DETAILED DESCRIPTION OF PREFERRED EMBODIMENT

Figure 2:
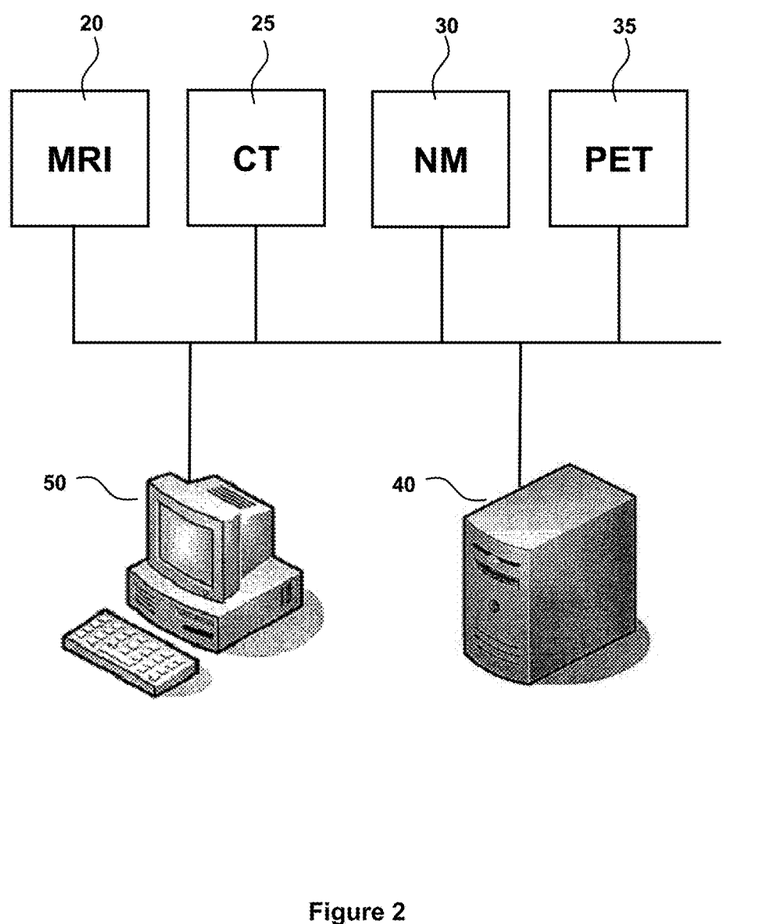
FIG. 2 is a block diagram showing a communication network including a number of scanners linked to a data storage system and a processing system.

The present invention is particularly applicable to dynamic MRI, CT, NM and PET imaging systems, for example dynamic MRI of the breast. Raw data and/or images collected by a scan, such as from a MRI scanner 20, CT scanner 25, NM scanner 30 or PET scanner 35 are forwarded to a data storage system 40 in the form of a Picture Archiving Communications System (PACS) in FIG. 2. A computer program operating on a processor 50, in the form of a computer, is used to retrieve or receive the various images or raw data from any one of the scanners 20, 25, 30 or 35 or from the data storage system 40. The program then processes those images to provide an improved data set for medical personnel to use, particularly in relation to evaluate both morphologic and kinetic information for diagnosis of disease and optimal discrimination between benign and malignant disease. The computer program need not reside on computer 50, but may reside in a console computer linked to any one of the scanners 20, 25, 30 or 35. Alternatively the program may reside in a workstation (stand-alone or in a system) or in the PACS 40.

The user will first use the computer software to instruct the computer processor or workstation 50 to load the dynamic image data into a memory of the computer processor 50. The processor may apply image registration to the data if it is applicable by configuration to a particular organ, such as of the brain, or by user instruction. Image registration is where images are aligned to account for motion correction in situations where a ROI of the subject moves due to respiratory or other functions of the subject. The processor then detects the pre-contrast baseline and the rapid initial enhancement phase, and converts the signal intensity profile of the data to the contrast enhancement profile depending on the type of image data loaded. The processor further detects a subject-dependent reference time-curve and then derives signature curves of enhancement patterns for a classification system. Thereafter automated classification and segmentation analyses are applied to a region of interest of the subject, such as a suspicious lesion in the breast. The results are then displayed on the processor to the user.

The method can be configured to apply a motion correction method depending on the specific function and organ being studied. A typical dynamic imaging data consisting of a series of 3-dimensional (3D) scans are acquired over a period of time. During acquisition, at least one scan is acquired before contrast injection and at least two scans after the injection. A dynamic imaging data acquisition usually takes several tens of seconds to several tens of minutes depending on the specific protocol used, and patient motion during the acquisition period can occur. To accurately evaluate the contrast enhancement patterns of different tissue types, image alignment or registration of the imaged volume over time is desired, particularly for accurate diagnosis of small-size lesions. Different kinds of motion correction method can be applied depending on the specific organ being studied. For example, a conventional rigid body image registration method can be applied automatically for the brain. However, for some body organs such as the breast, kidney or liver, non-uniform distortions are normally expected due to local tissue stretching associated with cardiac and/or respiratory motion. Some nonlinear motion compensation methods recognizable by persons skilled in the art may be used such as a non-rigid registration well known in medical imaging and remote sensing fields.

Figure 3:
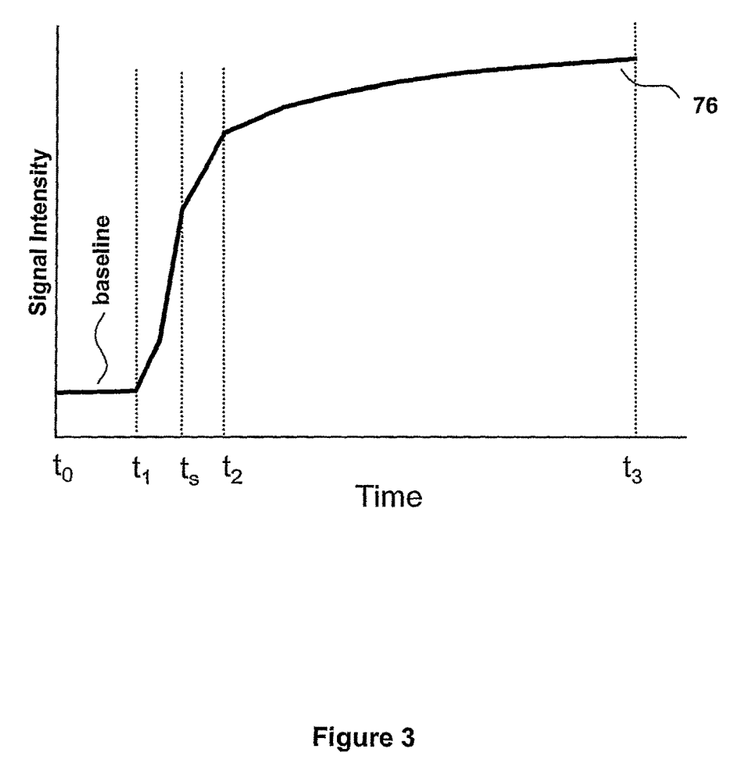
FIG. 3 is a plot of a typical averaged signal intensity time-curve from all pixels of a breast dynamic MRI data.

The process of detecting the pre-contrast baseline and the rapid initial enhancement phase involves the following steps of:

(1) Calculating the mean signal intensity of the entire volume at each time point to obtain a mean signal intensity time-curve S(t), as shown by 76 in FIG. 3;

(2) Estimating a mean enhancement time-curve $Y(t)=\Delta S=S(t)-S(t_0)$, where $t_0$ represents the time point for the first pre-contrast scan;

(3) Finding the maximum uptake slope at time point $t_s$ and the maximum enhancement $Y_{max}=\max\{Y(t)\}$;

(4) Searching backward from $t_s$ to find the first occurring time point $t_1$ such that $t_0 \leq t_1 \leq t_s$ and $Y(t_1) < a\% * Y_{max}$ where a % is used for example and the fraction value can be adjusted by configuration, such as 10%;

(5) Setting the initial enhancement period between $t_1$ and $t_2 = t_s + (t_s - t_1)$ and find the initial enhancement index time point at $t_2 > t_s$.

The process of further detecting a subject-dependent reference time-curve and derives signature enhancement patterns includes the following steps of:

(6) Calculating the mean baseline image $S_b(x, y, z)$ covering the time points from $t_0$ to $t_1$ for every pixel of (x, y, z) respectively;

(7) Calculating the initial enhancement index map as $Y_i(x, y, z)=S(x, y, z, t_2)-S_b(x, y, z)$ and the washout map as $Y_o(x, y, z)=S(x, y, z, t_2)-S(x, y, z, t_3)$, where $t_3$ represents the last time point of the dynamic data. Alternatively by configuration, the relative enhancement maps $Y_i(x, y, z)=S(x, y, z, t_2)/S_b(x, y, z)-1$ and $Y_o(x, y, z)=S(x, y, z, t_2)/S(x, y, z, t_3)-1$ can be used for the same purpose;

(8) Finding all the pixels collectively noted as XYZ satisfying the criteria of $Y_i(XYZ) > f * \max(Y_i)$ and $Y_o(XYZ) > 0$, where f can be adjusted as a masking threshold. For example, a reference time-curve $Y_{ref}(t)$ can be calculated by averaging those pixels with f=80% to represent the mean vascular enhancement profile with a strong and rapid initial uptake followed by late washout, as shown by the thick dotted curve 80 in FIG. 4.

Figure 4:
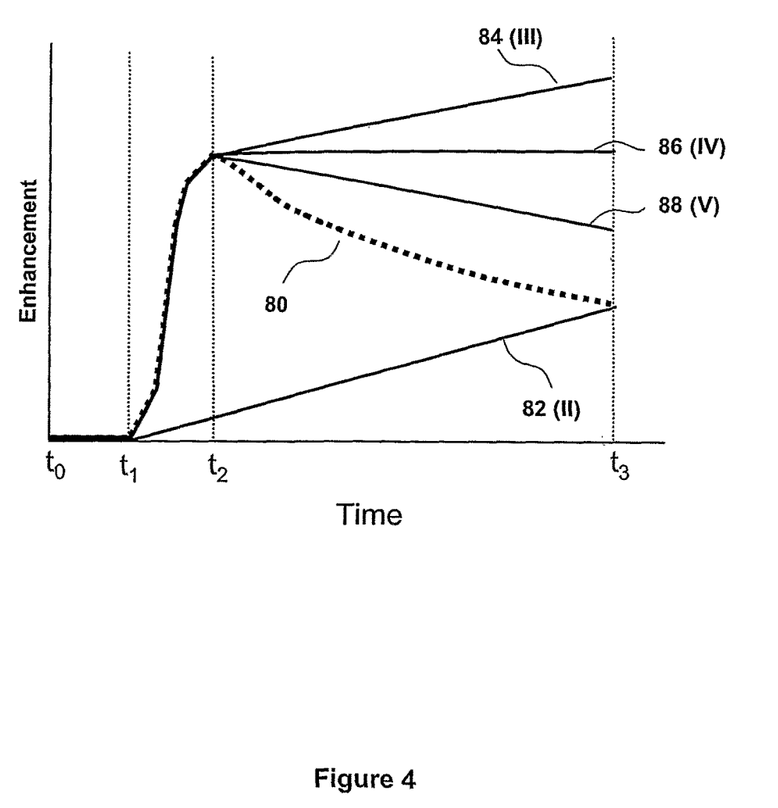
FIG. 4 is a series of plots showing a dotted line representing a typical vascular time-curve with rapid initial enhancement and fast washout, together with derived solid curves representing four types of signature enhancement curves as illustrated in FIG. 1.
Figure 5A:
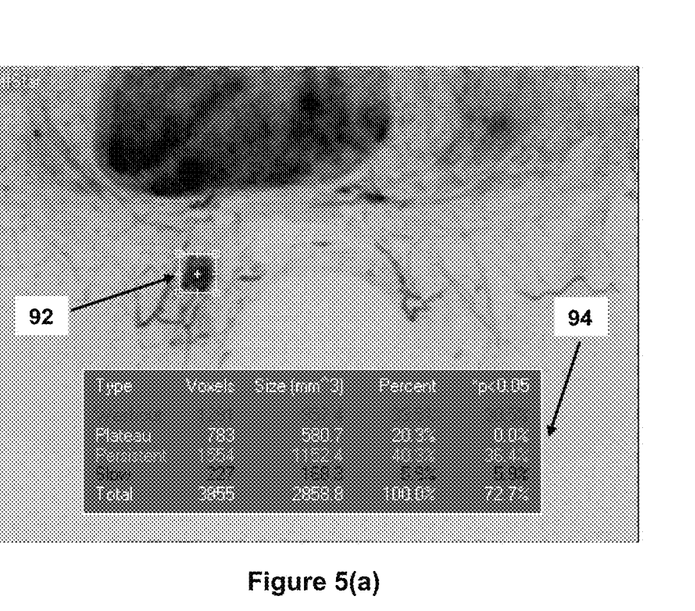
FIG. 5(a) shows a graphical interface displaying an enhancement index map in MIP mode.
Figure 5B:
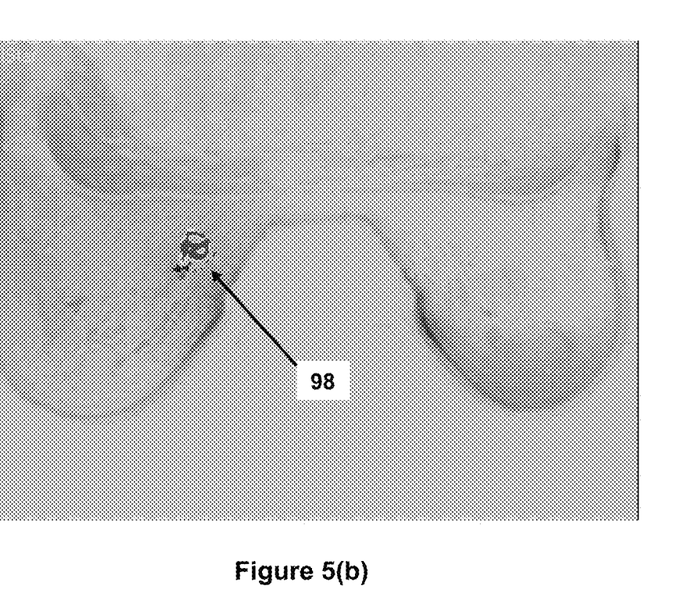
FIG. 5(b) shows a graphical interface displaying a color coded overlay of a pixel map of different types of enhancement curves on top of a raw image of a portion of the subject.
Figure 5C:
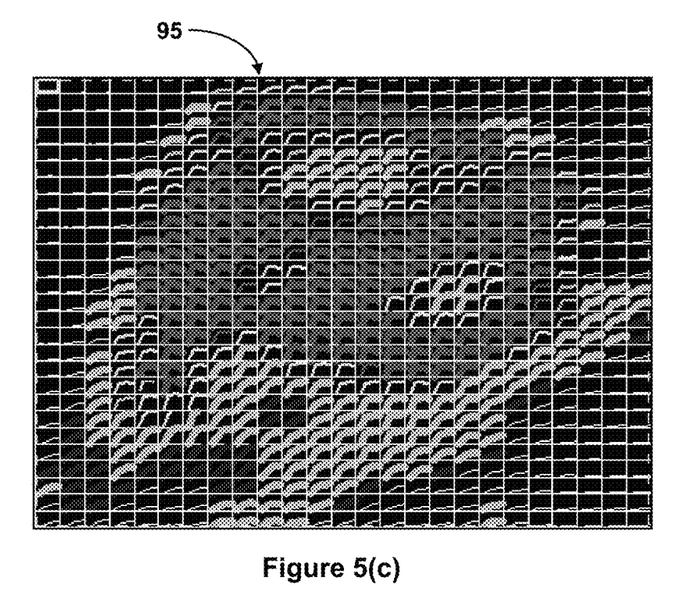
FIG. 5(c) is a gird-plot of curves for all pixels within the ROI of a displayed slice where different colors and line thicknesses are used to differentiate the enhancement curve type and whether it is statistically significant.
Figure 5D:
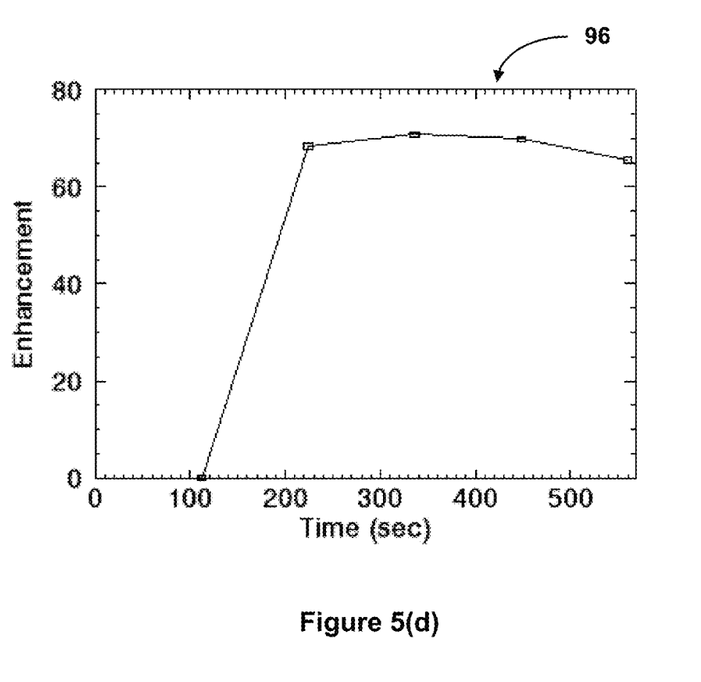
FIG. 5(d) is a plot of the mean enhancement curve of the ROI average signal intensity.

(9) Deriving four types of signature curves to represent the enhancement patterns as illustrated in FIG. 4 by:

$$Y_4(t) = \begin{cases} Y_{ref}(t) & (t \leq t_2) \\ Y_{ref}(t_2) & (t > t_2) \end{cases}$$

$$Y_5(t) = \begin{cases} Y_{ref}(t) & (t \leq t_2) \\ Y_{ref}(t_2) - \frac{1}{2}[Y_4(t_3) - Y_{ref}(t_3)](t - t_2)/(t_3 - t_2) & (t > t_2) \end{cases}$$

$$Y_3(t) = \begin{cases} Y_{ref}(t) & (t \leq t_2) \\ Y_{ref}(t_2) + \frac{1}{2}[Y_4(t_3) - Y_{ref}(t_3)](t - t_2)/(t_3 - t_2) & (t > t_2) \end{cases}$$

$$Y_2(t) = \begin{cases} 0 & (t \leq t_1) \\ Y_{ref}(t_3)(t - t_1)/(t_3 - t_1) & (t > t_1) \end{cases}$$

Where $Y_2(t)$ represents type II curve 82 with slow sustained enhancement (Slow), $Y_3(t)$ represents type III curve 84 with rapid initial and sustained late enhancement (Sustained/Persistent), $Y_4(t)$ represents type IV curve 86 with rapid initial and stable late enhancement (Plateau) and $Y_5(t)$ represents type V curve 88 with rapid initial and decreasing late enhancement (Washout).

The initial enhancement index time point ($t_2$) may be fixed by configuration for a specific data acquisition protocol. Further, the user may have the option to select a preferred time-curve from a pixel or a ROI, and set it as one of the signature curves described above.

The automated classification is applied to all pixels in a region of interest of the subject, such as a suspicious lesion in the breast. Pixels whose initial enhancement are below certain threshold (for example, $Y_i(XYZ)<10\%*max(Y_i)$ where the threshold percentage value can be adjusted by configuration) are classified as no enhancement type I and not included for further classification analysis. The time-curve of each candidate pixel is subject to a Spearman's rank correlation with each of the four signature curves ($Y_2$, $Y_3$, $Y_4$ and $Y_5$) to obtain correlation coefficients (cc) and statistical probability (p-value) respectively. The cc value ranges from −1 to 1, representing complete negative and positive linear relationships between two variables while a cc value of 0 means no linear relationship between the two variables. The smaller the p-value, the more significant the result is said to be. If the p-value is less than the significance level, the result is termed as statistically significant. The default level of significance (p value) is 5%, and the user can select other popular levels (1% or 0.1%) by configuration. For each pixel, a determination is made of the unique curve type corresponding to the maximum cc value. In the situation where multiple curve types produce the same maximum cc value, a further Pearson's correlation is applied to further determine the type also corresponding to the maximum Pearson's cc value. The classified curve type and corresponding p-value are recorded for each candidate pixel. The results are then displayed on the processor to the user.

The process of displaying the results involves an intuitive interface displaying the enhancement index map in MIP mode as shown in FIG. 5(*a*). The user can place a ROI 92 over a suspicious lesion on the MIP image. The processor automatically finds the slice containing the maximum amount of signal enhancement within the ROI, then display the detected slice. The processor further automatically detects a cluster of connected pixels belonging to one of the four signature types, and then calculates the volume of the cluster and the percentage contribution of each type with the results displayed in a tabular form 94 in the image window. The results of the segmentation and pattern classification of all pixels of the detected cluster can be stored in a color coded curve pattern map for display as a color overlay 98 on top of the raw image as shown in FIG. 5(*b*) for easy visualization of both the enhancement and morphology of the enhancing lesions. In addition, a grid-plot 95 of the curves for all individual pixels within the ROI of the displayed slice can be displayed simultaneously as shown in FIG. 5(*c*), wherein different colors and line-thickness can be used to highlight the type of enhancement curve and whether it is statistically significant for enhanced visual contrast effects. For example, each type of the four enhancing curves can be represented by different colors (e.g., red for type V, yellow for type IV, cyan for type III and blue for type II) while the line thickness differentiates whether the classification is significant (e.g., extra thick line for p<0.05 as being statistically significant versus thick line for non-significance), and the non-enhancing type I curve is marked by a white thin line. Alternatively, the user can display the mean curve-plot 96 of the ROI average signal intensity as shown in FIG. 5(*d*), which does not provide the enhancement heterogeneity information within as clearly shown by the grid-plot 95 in FIG. 5(*c*).

The user may have the option to apply the cluster analysis to each suspicious lesion highlighted by a ROI one by one, or to all lesions located within the boundary of a selected ROI.

Figure 6:
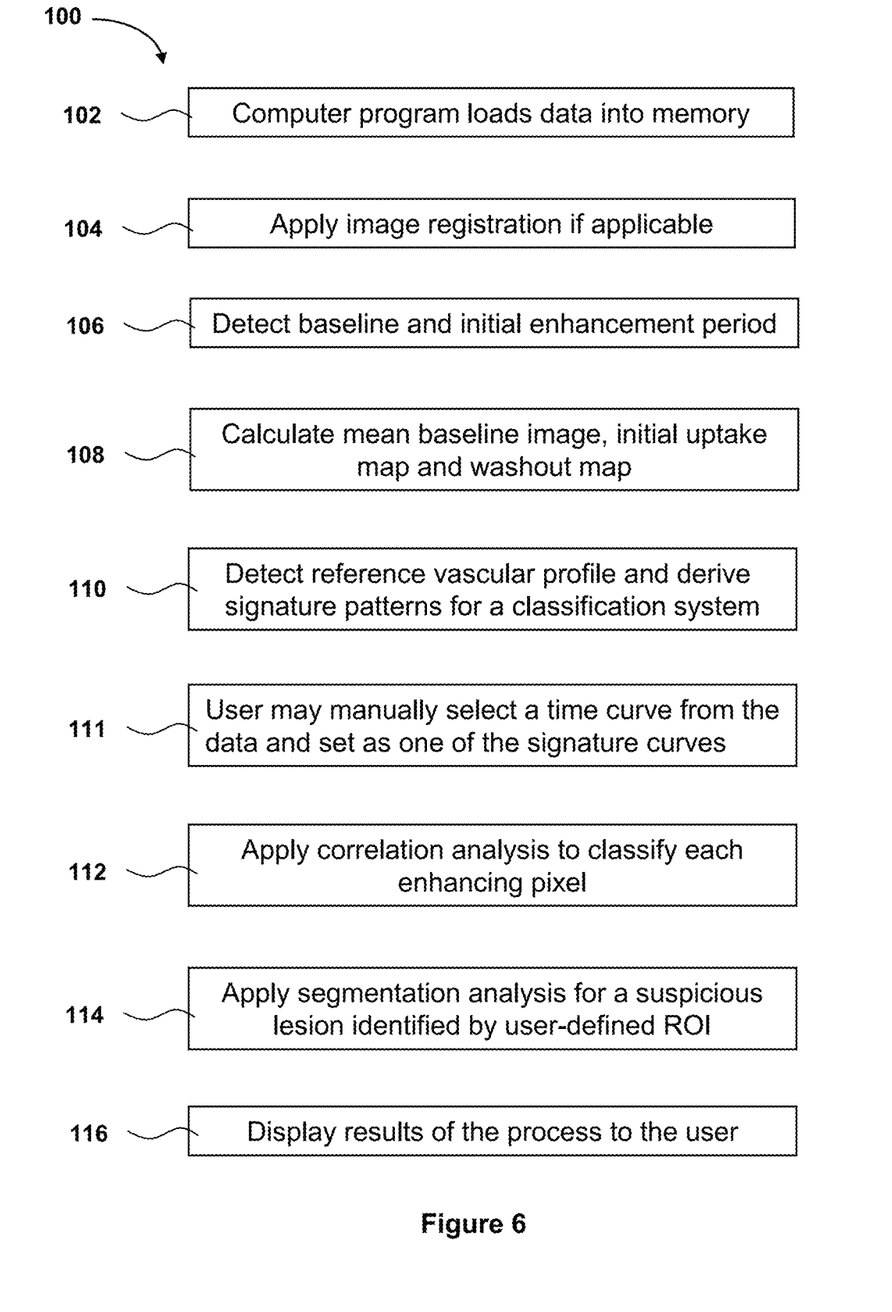
FIG. 6 is a flow diagram showing steps performed by a computer program to enable the processing of image data and display of results according to an embodiment of the invention.

With reference to FIG. 6 there is shown a flow diagram 100 of the steps taken by a computer program loaded into memory of a computer processor. Computer program code is written to perform the various steps and functions depicted in the flow diagram 100 whereby upon user instruction, the computer program loads the dataset into the memory of the computer processor at step 102. At step 104, if it is applicable to a particular scan, such as of the brain or breast, or by user instruction, image registration can be applied by the computer program. At step 106 the program detects the baseline and initial uptake/enhancement periods. At step 108 the mean baseline image, initial enhancement index map and washout map are calculated. At step 110 the computer program detects a reference curve from the mean vascular enhancement profile, and then derives the signature curves for a classification system. At step 111, the user may have the option to manually select a preferred time-curve from a pixel or a ROI to replace one of the signature curves detected. At step 112 a correlation analysis is applied to classify every pixel with initial enhancement above a certain threshold. At step 114, the program performs segmentation analysis of a suspicious lesion identified by a user-defined ROI and at 116 the results including a grid-plot and the color-coded curve pattern are then displayed of the whole process to the user for inspection and review.

This embodiment has been described using an example of a dynamic MRI of the breast. The invention is equally applicable to other disease such as prostate cancer, brain tumor or diseases in other body organs, not just of humans but animals as well, and using CT or NM or PET scans. Further the invention can be extended by combining the detailed kinetic and morphologic information in order to provide optimal discrimination between benign and malignant disease.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A method for automated classification of curve patterns associated with dynamic image data of a lesion in a subject in order to determine characteristics of the lesion by operating a computer program in a computer, comprising the steps of:
   (a) loading the image data into an electronic memory means;
   (b) producing a plot of signal intensity profile;
   (c) converting the signal intensity profile into a contrast enhancement profile;
   (d) before classifying a set of enhancement curves, detecting a subject-dependent reference vascular enhancement profile (RVE) $Y_{ref}(t)$ for an imaged volume, wherein the imaged volume includes different tissue types including lesion and non-lesion tissue by:
      i. calculating an initial enhancement index map $Y_i(x,y,z)$, and a washout map $Y_O(x,y,z)$ representing the decreasing profile portion, for every pixel (x,y,z) of the imaged volume;

ii. finding all pixels collectively noted as XYZ such that $Y_i(XYZ) > f*\max(Y_i)$ and $Y_O(XYZ) > 0$, where f is an adjustable masking threshold;
iii. calculating the RVE by averaging the contrast enhancement profiles from all pixels of XYZ with a predefined masking threshold value;

(e) deriving four signature curves representing enhancement curve patterns including slow, persistent, plateau and washout types based on the detected RVE for the subject and the following relationships:

$$Y_4(t) = \begin{cases} Y_{ref}(t) & (t \le t_2) \\ Y_{ref}(t_2) & (t > t_2) \end{cases}$$

$$Y_5(t) = \begin{cases} Y_{ref}(t) & (t \le t_2) \\ Y_{ref}(t_2) - \frac{1}{2}[Y_4(t_3) - Y_{ref}(t_3)](t - t_2)/(t_3 - t_2) & (t > t_2) \end{cases}$$

$$Y_3(t) = \begin{cases} Y_{ref}(t) & (t \le t_2) \\ Y_{ref}(t_2) + \frac{1}{2}[Y_4(t_3) - Y_{ref}(t_3)](t - t_2)/(t_3 - t_2) & (t > t_2) \end{cases}$$

$$Y_2(t) = \begin{cases} 0 & (t \le t_1) \\ Y_{ref}(t_3)(t - t_1)/(t_3 - t_1) & (t > t_1) \end{cases},$$

wherein $t_1$ and $t_2$ are start and end time points of an initial enhancement period respectively, and $t_3$ is a last time point of the image data;

(f) applying segmentation analysis to detect lesion pixels with initial enhancement magnitude greater than a predefined percentage of that of the RVE;

(g) applying a first correlation analysis to each enhancement curve of the set of enhancement curves corresponding to all detected lesion pixels respectively with the four signature curves to obtain a correlation coefficient value for the enhancement curve;

(h) classifying the enhancement curve corresponding to the maximum correlation coefficient value as a signature curve type that corresponds to the maximum correlation coefficient value; and (i) displaying a grid-plot of the classified enhancement curves for all individual pixels in a selected region of interest (ROI) for visualization of the distribution and heterogeneity of enhancement patterns corresponding to the characteristics of the lesion, wherein the enhancement curves in all pixels displayed in the grid-plot are highlighted by different color and line-thickness to reflect the type of enhancement curve and whether it is statistically significant respectively for visual identification.

2. A method according to claim 1 wherein prior to detecting a reference vascular enhancement profile, the method comprises the steps of detecting a pre-contrast baseline and the initial enhancement period by said computer program:

(a) calculating the mean signal intensity of the entire volume of contrast at each time point to obtain a mean signal intensity time-curve S(t);

(b) estimating a mean enhancement time-curve $Y(t) = S(t) - S(t_0)$, where t0 represents the time point for a first pre-contrast scan;

(c) finding a maximum uptake slope at time point $t_s$ and a maximum enhancement $Y_{max} = \max\{Y(t)\}$;

(d) searching backward from $t_s$ to find the first occurring time point $t_1$ such that $t_0 \le t_1 < t_s$ and $Y(t_1) < a\% * Y_{max}$ where a % is a fraction value that is adjustable; and (e) setting the initial enhancement period between $t_1$ and $t_2 = t_s + (t_s - t_1)$ and find an initial enhancement index time point at $t_2$.

3. A method according to claim 1 wherein the results of the segmentation analysis and curve classification include the lesion volume and the percentage contribution from pixels with each type of enhancement curves respectively.

4. A method according to claim 1 wherein the results of the segmentation analysis and curve classification of all pixels are stored in a color-coded curve pattern map for display as a color overlay on top of a raw image of the lesion.

5. A computer program embodied on a non-transitory computer-readable medium for automated classification of curve patterns associated with dynamic image data of a lesion in a subject, wherein the computer program instructs a processor to:

(a) load the image data into an electronic memory means;
(b) produce a plot of signal intensity profile;
(c) convert the signal intensity profile into a contrast enhancement profile;
(d) before classifying a set of enhancement curves, detect a subject-dependent reference vascular enhancement profile (RVE) $Y_{ref}(t)$ for an imaged volume, wherein the imaged volume includes different tissue types including lesion and non-lesion tissue by:
  i. calculating an initial enhancement index map $Y_i(x, y, z)$, and a washout map $Y_O(x,y,z)$ representing the decreasing profile portion, for every pixel (x,y,z) of the imaged volume;
  ii. finding all pixels collectively noted as XYZ such that $Y_i(XYZ) > f*\max(Y_i)$ and $Y_O(XYZ) > 0$, where f is an adjustable masking threshold;
  iii. calculating the RVE by averaging the contrast enhancement profiles from all pixels of XYZ with a predefined masking threshold value;
(e) derive four signature curves representing enhancement curve patterns including slow, persistent, plateau and washout types based on the detected RVE for the subject and the following relationships:

$$Y_4(t) = \begin{cases} Y_{ref}(t) & (t \le t_2) \\ Y_{ref}(t_2) & (t > t_2) \end{cases}$$

$$Y_5(t) = \begin{cases} Y_{ref}(t) & (t \le t_2) \\ Y_{ref}(t_2) - \frac{1}{2}[Y_4(t_3) - Y_{ref}(t_3)](t - t_2)/(t_3 - t_2) & (t > t_2) \end{cases}$$

$$Y_3(t) = \begin{cases} Y_{ref}(t) & (t \le t_2) \\ Y_{ref}(t_2) + \frac{1}{2}[Y_4(t_3) - Y_{ref}(t_3)](t - t_2)/(t_3 - t_2) & (t > t_2) \end{cases}$$

$$Y_2(t) = \begin{cases} 0 & (t \le t_1) \\ Y_{ref}(t_3)(t - t_1)/(t_3 - t_1) & (t > t_1) \end{cases},$$

wherein $t_1$ and $t_2$ are start and end time points of an initial enhancement period respectively, and $t_3$ is a last time point of the image data;

(f) apply segmentation analysis to detect lesion pixels with initial enhancement magnitude greater than a predefined percentage of that of the RVE;

(g) apply a first correlation analysis to each enhancement curve of the set of enhancement curves corresponding to all detected lesion pixels respectively with the four signature curves to obtain a correlation coefficient value for the enhancement curve;

(h) classifying the enhancement curve corresponding to the maximum correlation coefficient value as a signature curve type that corresponds to the maximum correlation coefficient value; and (i) display a grid-plot of the classified enhancement curves for all individual pixels in a selected region of interest (ROI) for visualization of the distribution and heterogeneity of enhancement patterns corresponding to the characteristics of the lesion, wherein the enhancement curves in all pixels displayed in the grid-plot are highlighted by different color and line-thickness to reflect the type of enhancement curve and whether it is statistically significant respectively for visual identification.

6. A system for automated classification of curve patterns associated with dynamic image data of a lesion in a subject in order to determine characteristics of the lesion, the system comprising:

A scanner for providing a dynamic image scan of the subject;

A processor linked to the scanner for retrieving the image data from the scan;

the processor further configured to execute a computer program in a computer that:

(a) loads the image data into an electronic memory means;
(b) produces a plot of signal intensity profile;
(c) converts the signal intensity profile into a contrast enhancement profile;
(d) before classifying a set of enhancement curves, detects a subject-dependent reference vascular enhancement profile (RVE) $Y_{ref}(t)$ for an imaged volume, wherein the imaged volume includes different tissue types including lesion and non-lesion tissue by:
  i. calculating an initial enhancement index map $Y_i(x,y,z)$, and a washout map $Y_O(x,y,z)$ representing the decreasing profile portion, for every pixel $(x,y,z)$ of the imaged volume,
  ii. finding all pixels collectively noted as XYZ such that $Y_i(XYZ) > f*\max(Y_i)$ and $Y_O(XYZ) > 0$, where f is an adjustable masking threshold;
  iii. calculating the RVE by averaging the contrast enhancement profiles from all pixels of XYZ with a predefined masking threshold value;
(e) derives four signature curves representing typical enhancement curve patterns including slow, persistent, plateau and washout types based on the detected RVE for the subject and the following relationships:

$$Y_4(t) = \begin{cases} Y_{ref}(t) & (t \le t_2) \\ Y_{ref}(t_2) & (t > t_2) \end{cases}$$

$$Y_5(t) = \begin{cases} Y_{ref}(t) & (t \le t_2) \\ Y_{ref}(t_2) - \frac{1}{2}[Y_4(t_3) - Y_{ref}(t_3)](t-t_2)/(t_3-t_2) & (t > t_2) \end{cases}$$

$$Y_3(t) = \begin{cases} Y_{ref}(t) & (t \le t_2) \\ Y_{ref}(t_2) + \frac{1}{2}[Y_4(t_3) - Y_{ref}(t_3)](t-t_2)/(t_3-t_2) & (t > t_2) \end{cases}$$

$$Y_2(t) = \begin{cases} 0 & (t \le t_1) \\ Y_{ref}(t_3)(t-t_1)/(t_3-t_1) & (t > t_1) \end{cases},$$

wherein $t_1$ and $t_2$ are start and end time points of an initial enhancement period respectively, and $t_3$ is a last time point of the image data;

(f) applies segmentation analysis to detect lesion pixels with initial enhancement magnitude greater than a predefined percentage of that of the RVE;

(g) applies a first correlation analysis to each enhancement curve of the set of enhancement curves corresponding to all detected lesion pixels respectively with the four signature curves to obtain a correlation coefficient value for the enhancement curve;

(h) classifying the enhancement curve corresponding to the maximum correlation coefficient value as a signature curve type that corresponds to the maximum correlation coefficient value; and (i) displays a grid-plot of the classified enhancement curves for all individual pixels in a selected region of interest (ROI) for direct visualization of the distribution and heterogeneity of detailed enhancement patterns corresponding to the characteristics of the lesion, wherein the enhancement curves in all pixels displayed in the grid-plot are highlighted by different color and line-thickness to reflect the type of enhancement curve and whether it is statistically significant respectively for visual identification.

7. A system according to claim 6 wherein prior to detecting a reference vascular enhancement profile, the processor detects a pre-contrast baseline and the initial enhancement period comprising the steps of:

(a) calculating the mean signal intensity of the entire volume of contrast at each time point to obtain a mean signal intensity time-curve $S(t)$;
(b) estimating a mean enhancement time-curve $Y(t) = S(t) - S(t_0)$, where $t_0$ represents the time point for a first pre-contrast scan;
(c) finding a maximum uptake slope at time point ts and a maximum enhancement $Y_{max} = \max\{Y(t)\}$;
(d) searching backward from $t_s$ to find the first occurring time point $t_1$ such that $t_0 \le t_1 < t_s$ and $Y(t_1) < a\% * Y_{max}$ where a % is a fraction value that is adjustable; and
(e) setting the initial enhancement period between $t_1$ and $t_2 = t_s + (t_s - t_1)$ and find an initial enhancement index time point at $t_2$.

8. A system according to claim 6 wherein the results of the segmentation analysis and curve classification include the lesion volume and the percentage contribution from pixels with each type of enhancement curves respectively.

9. A method according to claim 1 wherein prior to classifying an enhancement curve, the method further comprises the steps of selecting an enhancement curve from a pixel or a ROI, and setting it as one of the signature curves for the purpose of correlation analysis.

10. A system according to claim 6 wherein prior to the processor classifying an enhancement curve further comprises the steps of the processor selecting an enhancement curve from a pixel or a ROI, and setting it as one of the signature curves for the purpose of correlation analysis.

11. A method according to claim 1 wherein the correlation analysis includes a rank correlation with respect to the signature curves in order to obtain correlation coefficients and statistical p-values.

12. A system according to claim 6 wherein the correlation analysis includes a rank correlation with respect to the signature curves in order to obtain correlation coefficients and statistical p-values.

13. A method according to claim 1 further comprising performing a second correlation analysis that differs from the first correlation analysis when multiple enhancement curves correspond to the same maximum coefficient value.

14. A system according to claim 6 wherein the processor is further configured to perform a second correlation analysis that differs from the first correlation analysis when multiple enhancement curves correspond to the same maximum coefficient value.

\* \* \* \* \*